(12) United States Patent
Godara

(10) Patent No.: US 8,361,063 B2
(45) Date of Patent: Jan. 29, 2013

(54) SYSTEM AND METHOD FOR CONTROLLING ENERGY DELIVERY

(75) Inventor: Neil Godara, Mississauga (CA)

(73) Assignee: Kimberly-Clark Inc., Ontario (CA)

( * ) Notice: Subject to any disclaimer, the term of this patent is extended or adjusted under 35 U.S.C. 154(b) by 1642 days.

(21) Appl. No.: 11/622,668

(22) Filed: Jan. 12, 2007

(65) Prior Publication Data

US 2007/0118191 A1 May 24, 2007

Related U.S. Application Data

(63) Continuation-in-part of application No. 10/864,410, filed on Jun. 10, 2004, now Pat. No. 7,163,536.

(51) Int. Cl.
*A61B 18/04* (2006.01)

(52) U.S. Cl. ................ 606/34; 606/41; 606/42

(58) Field of Classification Search .............. 606/32–50; 607/96–114
See application file for complete search history.

(56) References Cited

U.S. PATENT DOCUMENTS

| | | | |
|---|---|---|---|
| 4,244,371 A | 1/1981 | Farin | |
| 5,334,193 A | 8/1994 | Nardella | |
| 5,462,521 A | 10/1995 | Brucker et al. | |
| 5,688,267 A | 11/1997 | Panescu et al. | |
| 5,788,688 A | 8/1998 | Bauer et al. | |
| 5,800,432 A | 9/1998 | Swanson | |
| 6,017,338 A | 1/2000 | Brucker et al. | |
| 6,053,912 A | 4/2000 | Panescu et al. | |
| 6,165,169 A | 12/2000 | Panescu et al. | |
| 6,235,022 B1 | 5/2001 | Hallock et al. | |
| 6,273,886 B1 | 8/2001 | Edwards et al. | |
| 6,500,175 B1 | 12/2002 | Gough et al. | |
| 6,506,189 B1 | 1/2003 | Rittman, III et al. | |
| 6,575,969 B1 | 6/2003 | Rittman, III et al. | |
| 6,623,423 B2 | 9/2003 | Sakurai et al. | |
| 6,679,875 B2 | 1/2004 | Honda et al. | |
| 6,702,810 B2 | 3/2004 | McClurken et al. | |
| 6,783,523 B2 * | 8/2004 | Qin et al. | 606/1 |
| 6,830,569 B2 | 12/2004 | Thompson et al. | |
| 6,899,538 B2 | 5/2005 | Matoba | |
| 6,936,047 B2 | 8/2005 | Nasab et al. | |
| 6,939,346 B2 | 9/2005 | Kannenberg et al. | |
| 7,137,980 B2 * | 11/2006 | Buysse et al. | 606/34 |
| 7,217,269 B2 | 5/2007 | El-Galley et al. | |
| 8,012,150 B2 * | 9/2011 | Wham et al. | 606/38 |
| 2004/0054365 A1 | 3/2004 | Gobie | |
| 2005/0137662 A1 | 6/2005 | Morris et al. | |
| 2006/0161148 A1 | 7/2006 | Behnke | |

FOREIGN PATENT DOCUMENTS

| | | |
|---|---|---|
| DE | 43 39 049 | 5/1995 |
| DE | 10 2005 00776 | 8/2006 |
| EP | 1 472 984 | 4/2004 |
| WO | WO 2005/107857 | 11/2005 |

* cited by examiner

*Primary Examiner* — Roy Gibson

(74) *Attorney, Agent, or Firm* — Dority & Manning, P.A.

(57) ABSTRACT

Embodiments of the present invention provide systems and methods for controlling energy delivery by mapping one or more devices capable of delivering energy, for example energy capable of modulating one or more properties of a tissue, to one or more sources of the energy or to one or more measuring devices. In some embodiments, associations between these components are determined by delivering energy through the energy sources and measuring a response using the measuring devices.

35 Claims, 6 Drawing Sheets

SYSTEM AND METHOD FOR CONTROLLING ENERGY DELIVERY

This application claims priority from and is a continuation-in-part of U.S. patent application Ser. No. 10/864,410, filed Jun. 10, 2004, now U.S. Pat. No. 7,163,536 incorporated herein by reference.

TECHNICAL FIELD

The invention relates generally to the field of energy delivery-based surgery. More particularly, the invention relates to systems and methods for controlling the delivery of energy from at least one energy source to at least one energy delivery device.

BACKGROUND OF THE ART

When a system used to deliver energy to a tissue comprises more than one energy delivery device, energy source or measuring device, it is useful for the connections between the energy delivery devices, energy sources and measurement devices to be known. That is to say, because energy delivery may be controlled based on values provided by measuring devices associated with the energy delivery devices, it is useful to know which energy sources are capable of providing energy to the energy delivery devices capable of affecting the given measurement. Incorrect mapping, which is a failure to correctly recognize which energy delivery devices correspond to which energy sources, can result in the delivery of energy through an energy delivery device other than that intended to be used, resulting in an unintended change in a tissue property.

In order to prevent such problems, some current treatment systems use connectors that are colour coded, which have mating parts, or which are otherwise designed so that each energy delivery device is connected only to certain energy sources. This approach takes time to connect and to check, and requires that unique connectors be used for each pair or group of devices and sources to be connected. The use of unique connectors can reduce convenience or increase cost for the user or manufacturer, for example by requiring that a variety of parts be designed, manufactured and kept in stock. As well, visual matching of energy sources to energy delivery devices does not necessarily preclude improper connections from being made.

Therefore, it would be desirable to provide systems and methods that allow for unknown connections between energy sources, delivery devices and measuring devices, to be determined.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Figure 1:
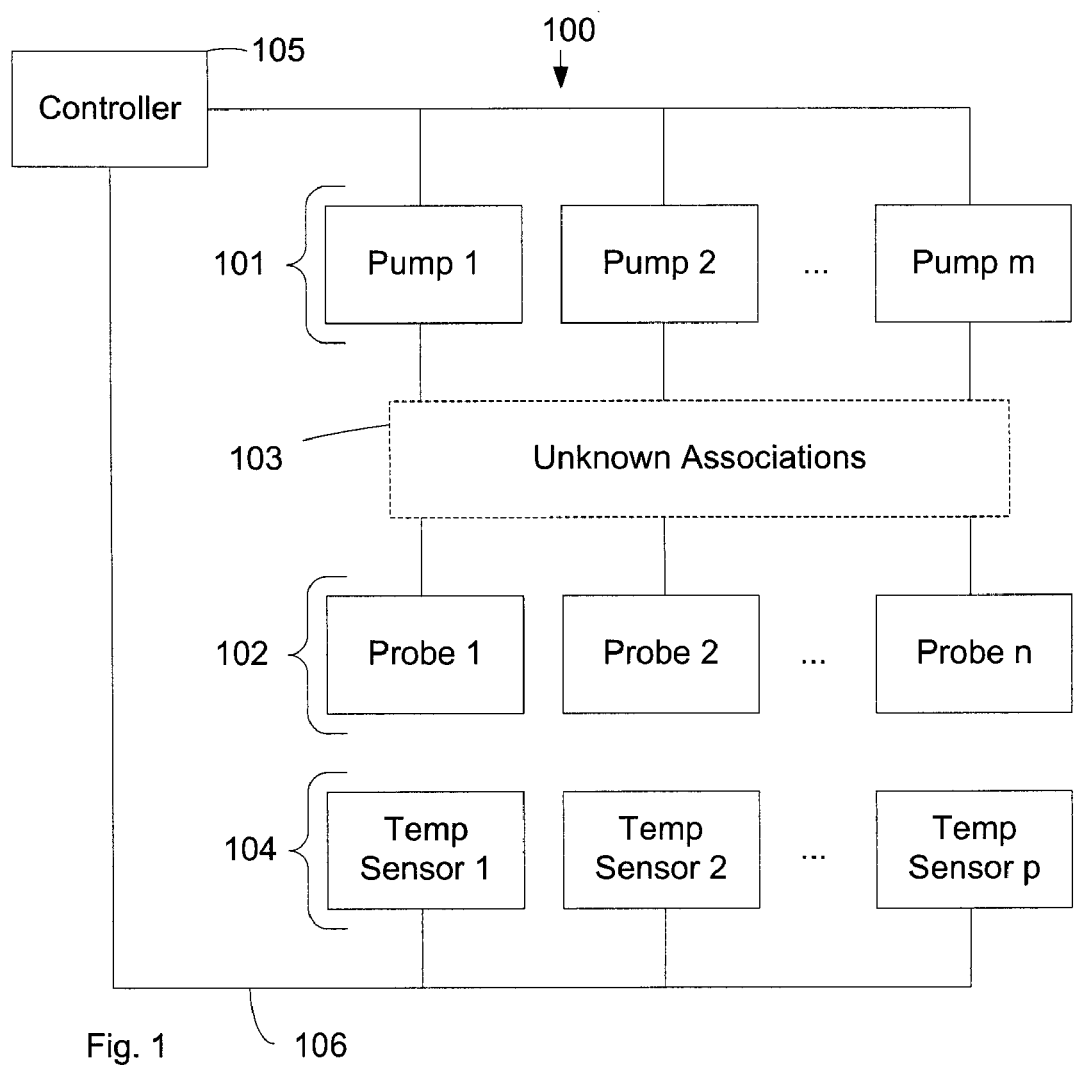
FIG. 1 is a block diagram showing components of a system in accordance with an exemplary embodiment of the invention.

Embodiments of the present invention provide systems and methods for controlling energy delivery by mapping one or more devices capable of delivering energy, for example energy capable of modulating one or more properties of a tissue, to one or more sources of the energy or to one or more measuring devices.

In accordance with one broad aspect, embodiments of the present invention provide a system for controlling the delivery of energy from at least one energy source to at least one energy delivery device, the system comprising: an energy source interface for controlling the delivery of energy from the at least one energy source; a measuring interface for receiving measurements indicating a change in a property of a tissue; and a mapping subsystem capable of determining an unknown association between at least one energy delivery device and one of the at least one energy source and the at least one measuring device.

In accordance with a further broad aspect, embodiments of the present invention provide a system for delivering energy, the system comprising: at least one energy source, each energy source capable of producing energy according to an output profile that is distinct from the output profiles of each other energy source; at least one energy delivery device, each delivery device operatively coupled to one or more of the energy sources for delivering the energy; at least one measuring device for measuring changes in a property of a tissue; and a controller operatively coupled to the at least one measuring device and to the at least one energy source for controlling the at least one source and for determining an association between each energy delivery device and one of the at least one energy source and the least one measuring device by analyzing the changes.

In accordance with a broad method aspect, embodiments of the present invention provide a method for controlling delivery of energy from at least one energy source to a tissue via at least one energy delivery device operatively coupled to the at least one energy source, the method comprising: delivering energy from the at least one energy source; obtaining measurements indicating changes in a property of the tissue using at least one measuring device to determine at least one response profile; and analyzing the at least one response profile to determine an unknown association between the at least one energy delivery device and one of the at least one energy source and the at least one measuring device, thereby to control the delivery of energy to the tissue.

With specific reference now to the drawings in detail, it is stressed that the particulars shown are by way of example and for purposes of illustrative discussion of some embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 6A:
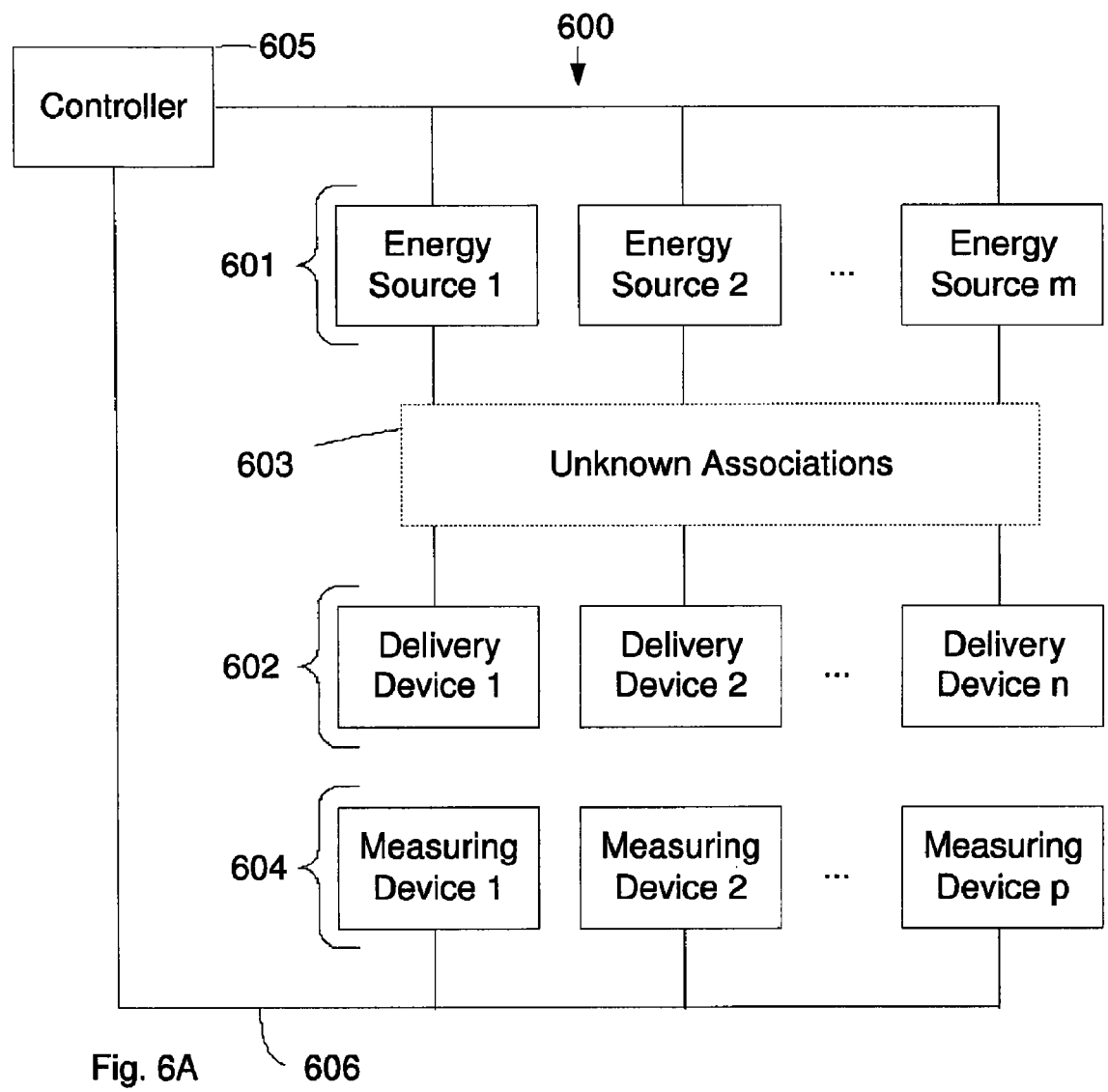
FIG. 6A is a block diagram showing components of a system in accordance with one general embodiment of the invention.
Figure 6B:
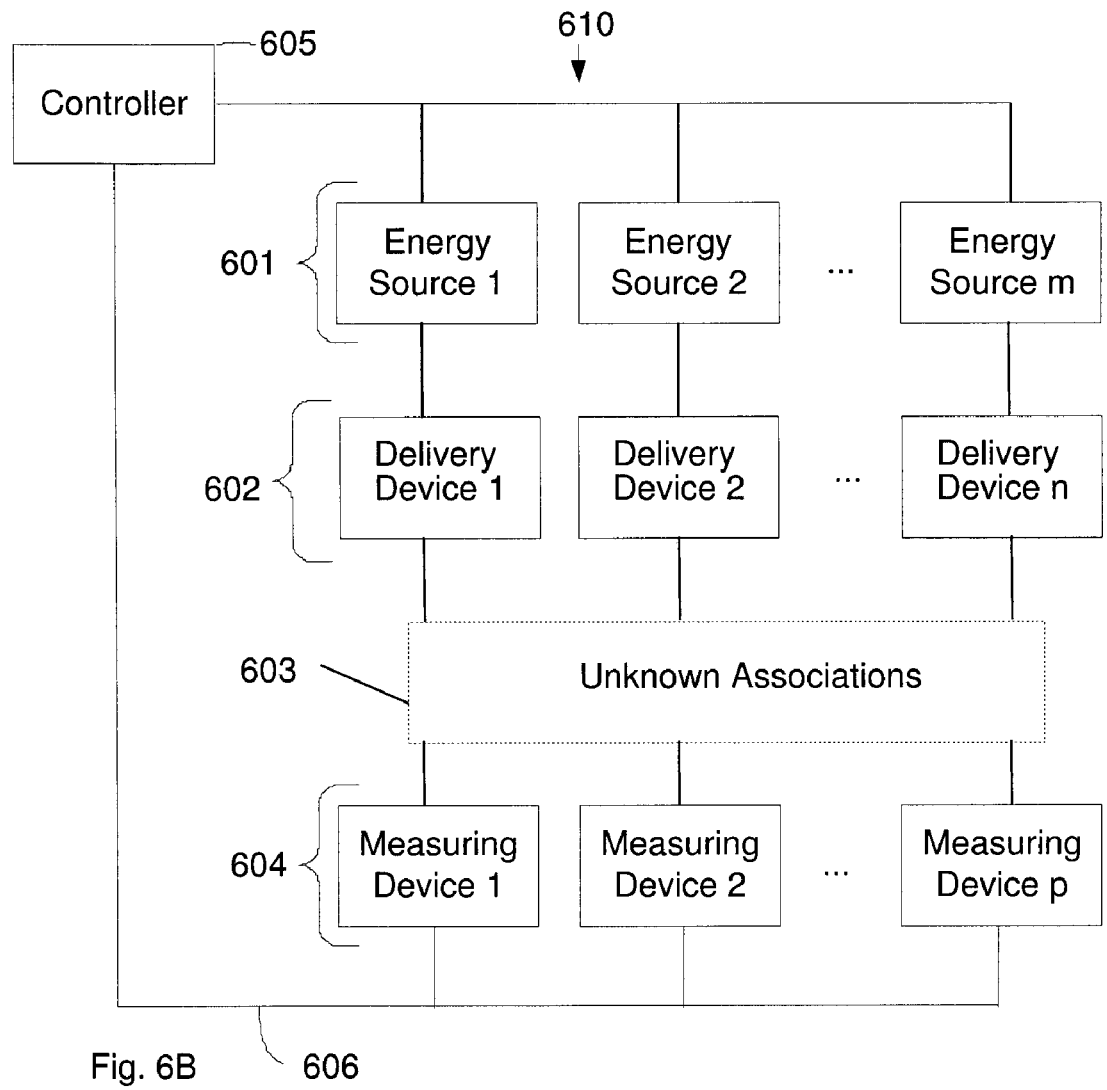
FIG. 6B is a block diagram showing components of a system in accordance with an alternate general embodiment of the invention.

Prior to describing general embodiments of the present invention, as illustrated in FIGS. 6A and 6B, and for ease of explaining typical structures and functions of embodiments of the present invention, a specific exemplary embodiment will be presently described. Thus, with reference first to FIG. 1, an exemplary embodiment of one broad aspect of the present invention is shown. In this particular embodiment, a system 100 comprises one or more pumps 101 to control the movement of a cooling fluid medium which is capable of removing thermal energy from one or more internally cooled probes 102, or from tissue surrounding the probe(s). In this embodiment, probe(s) 102 are capable of being inserted into the body of a patient, either directly or indirectly, for example by using an introducer or other means for insertion. In the context of the present invention, although the pumps 101 are used to remove thermal energy, their purpose may be generalized as energy sources, such as energy sources 601 shown in a general embodiment of the invention in FIG. 6A, in that they are capable of working to change the energy of a probe 102 or tissue.

In this embodiment, pumps 101 are coupled to probes 102 via releasable connections 103. In this embodiment, each connection 103 typically comprises a tube or other conduit for carrying the cooling medium and at least one end of the tube has a connector adapted for releasable connection to a probe 102 or a pump 101. The other end may have a releasable connection for attaching to the other of the pump and the probe; however, this connection may be fixed. In accordance with a particular arrangement of an aspect of the invention, connections 103 are unknown and may be determined using embodiments of the present invention, as described herein.

Cooling fluid supplied by pumps 101 circulates within probes 102, which can thus be understood to be energy delivery devices, such as devices 602 of the general embodiment shown in FIG. 6A. In some particular embodiments, the probes 102 are furnished with electrodes or other heating elements for ablating tissue.

In the embodiment of FIG. 1, the probes 102 are associated with temperature sensors 104, which may be carried by the probes 102 themselves, or may be self-contained and separate from the probes 102, so long as the sensors 104 are capable of sensing changes in temperature caused by the removal of thermal energy by or from the probes 102. In one particular embodiment, temperature sensors 104 comprise thermocouples directly coupled to the probes 102. For example, the thermocouples may be soldered and/or welded to probe 102.

In this embodiment, the temperature sensors 104 are connected, via electrical connections 106 to a central controller 105, which receives and analyzes the temperature information. In this particular embodiment, the associations between temperature sensors 104 and probes 102 are known. In other words, it is known which sensors 104 are capable of sensing changes in temperature caused by which probes. In an alternate embodiment, described further herein below, these associations are not known and may be determined using embodiments of a method of the present invention.

Figure 2:
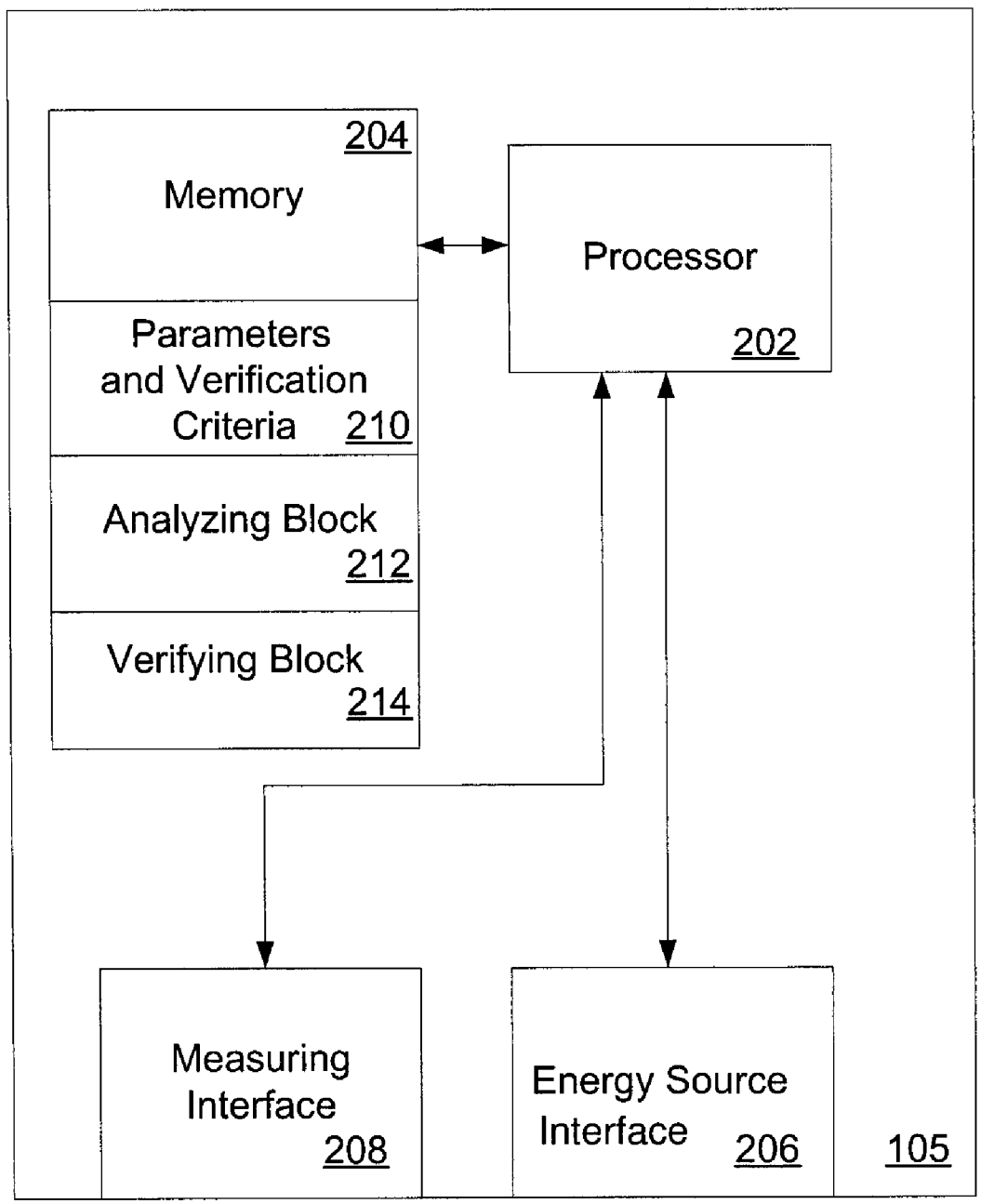
FIG. 2 is a block diagram of an exemplary controller in accordance with an embodiment of the invention.

The controller 105 is responsible for controlling the operation of the pumps 101 in accordance with output profiles. Controller 105 operates the pumps 101 to modify the output profile based on temperature information received from the temperature sensors 104. FIG. 2 is a block diagram of a software programmable embodiment of a controller 105. In this embodiment, controller 105 comprises a processor 202 coupled to a memory store 204 (for example, a ROM, a RAM, a flash memory device or a combination thereof) which stores instructions and data for controlling the operations of processor 202. Processor 202 is also coupled to an energy source interface 206 for controlling pumps 101 and to a measuring interface 208 for receiving temperature measurements from temperature sensors 104.

Memory 204 stores instructions for performing analyzing operations (analyzing block 212) to determine unknown associations and for verifying the analysis results (verifying block 214), as well as data such as tuneable parameters and thresholds and verification criteria 210 for use by the instructions 212, 214. In this embodiment, analyzing block 212 comprises instructions for adapting the processor to associate at least one probe 102 with at least one pump 101 in response to an analysis of a response profile determined using a sensor 104. For example, the response profile may define a change in temperature measured by a sensor 104 and the analyzing block 212 may comprise instructions for matching the output profiles of pumps 101 and the response profile(s) of sensors 104.

Thus, processor 202, in conjunction with memory 204, comprises a mapping subsystem capable of determining an unknown association between probes 102 and pumps 101. The process of determining the unknown association is described further herein below. Persons of ordinary skill in the art will appreciate that additional instructions may also be present (not shown) such as one or more of an operating system, a communication system and user interface instructions, among others. As well, controller 105 may additionally comprise components such as one or more I/O interfaces, power sources, etc. In some embodiments of the present invention, controller 105 is contained within a single device.

In the system 100 described above, the connections 103 between pumps 101 and probes 102 are not permanent. This flexibility allows for a variable number of pumps 101 and a variable number of probes 102 to be used, and allows for any pump 101 to be connected to one or more probes 102 or for any probe 102 to be connected to one or more pumps 101. Because these connections are not permanent, a determination must be made, prior to treatment, of the specific configuration of the system so that if a region of tissue capable of being cooled by a certain probe 102 requires cooling during treatment, controller 105 can operate an appropriate pump 101 capable of supplying cooling fluid to that probe 102. While the present system can be used in conjunction with tubing 103 that visually indicates (for example, by using colour), or physically restricts (for example by using shaped mating connectors) the connections, it is also intended to be able to be used as the sole mode of determining the connections between pumps 101 and probes 102.

In order to describe the operation of system 100 of the exemplary embodiment described above, a particular embodiment of a method aspect of the present invention is provided herein. As mentioned earlier with respect to FIG. 1, a general embodiment of a method aspect of the present invention is further provided herein below and illustrated in FIG. 7.

Figure 3:
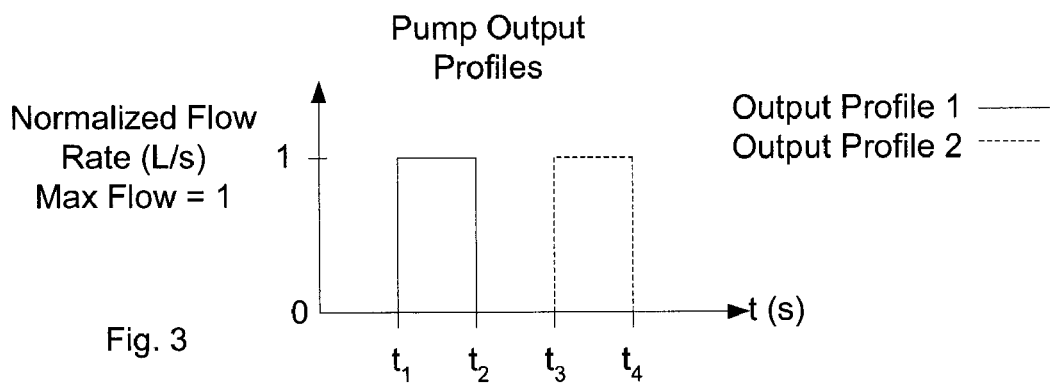
FIG. 3 is an exemplary graph showing two output profiles that may be produced in accordance with an embodiment of the invention.
Figure 4:
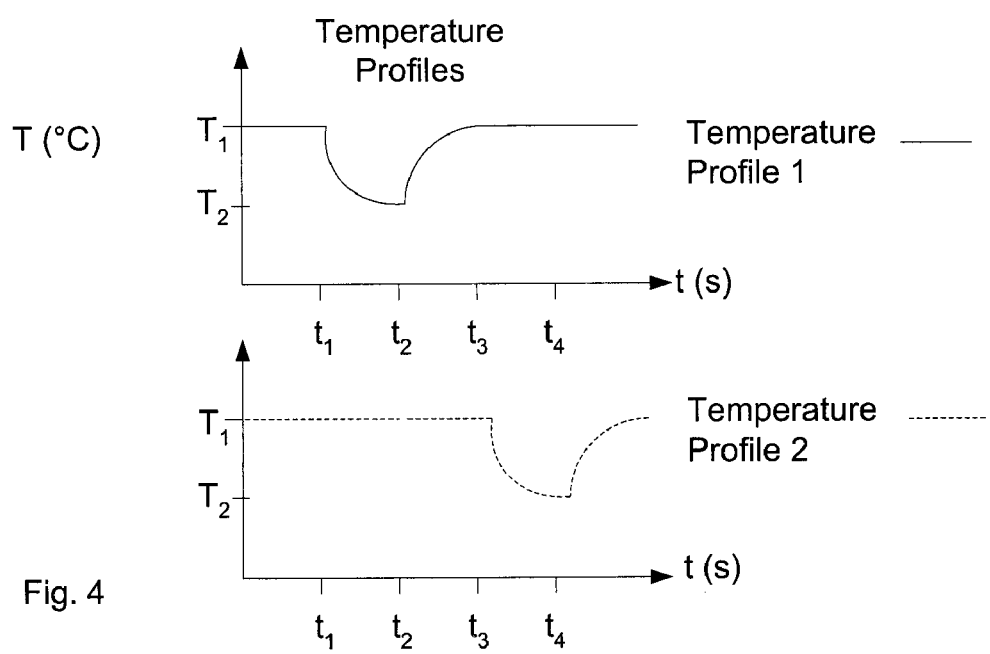
FIG. 4 is an exemplary graph showing two temperature profiles, which correspond to the output profiles of FIG. 3, and which may be produced in accordance with an embodiment of the invention.

In operation, and in order to determine connections 103 between pumps 101 and probes 102, the controller 105 sends a signal to modify a pump flow rate to produce a specific output profile. As shown in FIG. 3, the shape of the output profile is a representation of a pump's flow rate with respect to time. Each pump 101 pumps cooling fluid according to its respective output profile. The temperatures of the probes 102, measured by sensors 104, change correspondingly. The changes in temperature over time produce a characteristic shape, or temperature profile, also referred to more generally as a response profile. FIG. 4 shows possible temperature profiles that correspond to the output profiles shown in FIG. 3. The temperature profile is measured by one or more temperature sensors 104 and is communicated to the controller 105 through electrical connections 106. A variable number of temperature sensors 104 may be used to detect the temperature profile of a probe 102. As well, one temperature sensor 104 may be used to detect the temperature profiles of more than one probe 102. However, in this embodiment, in order for mapping to occur, it is necessary that the relationships between temperature sensors 104 and probes 102 be known, so that any match made between the temperature profile measured by a temperature sensor 104 and an output profile produced by one or more pumps 101 will necessarily correspond to a relationship between particular probe or probes 102 and particular pump or pumps 101. This matched relationship represents a mapping of probes 102 to pumps 101. In one particular embodiment of system 100, individual temperature sensors 104 are directly coupled to respective probes 102 giving a known and permanent relationship for the purposes of mapping. In an alternate embodiment, described herein below, the relationships between the measuring devices and the energy delivery devices are not known, and may be determined in accordance with embodiments of the present invention.

In further embodiments, various output profiles may be utilized, as long as each pump is capable of producing an output profile that is distinct from the output profiles of any other pumps and will result in response profiles that are distinguishable from one another. In some embodiments, for example as described hereinabove, each pump is operated at least partially sequentially, such that the output profiles are temporally distinguishable from each other. In other embodiments, the pumps are operated substantially concurrently, such that the output profiles may be temporally indistinguishable. In such embodiments, in order to distinguish between the output profiles, one or more parameters may be modified. For example, one pump may be operated at a lower flow rate than another pump, such that the respective response profile would be expected to show less of a change in temperature. Alternatively, one or more pumps may be operated with a variable flow rate, with the rate of change of temperature in the response profile corresponding to the rate of change of flow rate in the output profile. In yet further embodiments, for example where the system is operable to control the temperature of a cooling medium delivered by the pumps, the temperature of a cooling fluid in one pump may be lower than in another pump, such that the output profiles, in this case referring to the temperature of the cooling medium over time, are distinguishable and will result in distinguishable response profiles. In embodiments of the invention wherein the energy sources are not pumps, other parameters may be modified in order to produce distinct output profiles. For example, in embodiments wherein the energy sources comprise one or more electrosurgical generators, one or more of voltage, current and power may be modified.

As will be described further herein below, controller 105 is capable of performing an analysis to match temperature response profiles and pump output profiles. In some embodiments, such an analysis may be directed by software stored, for example in analyzing block 212, or otherwise communicatively coupled to controller 105. The analysis may be adjusted or tuned through variable tolerances, which may be manually or automatically tuned to control matching. For example, for any given output profile, the tolerances for: magnitude of temperature change for any given change in flow rate, delay before change is observed, and, rate at which change occurs, are among the tolerances that can be controlled.

Figure 5:
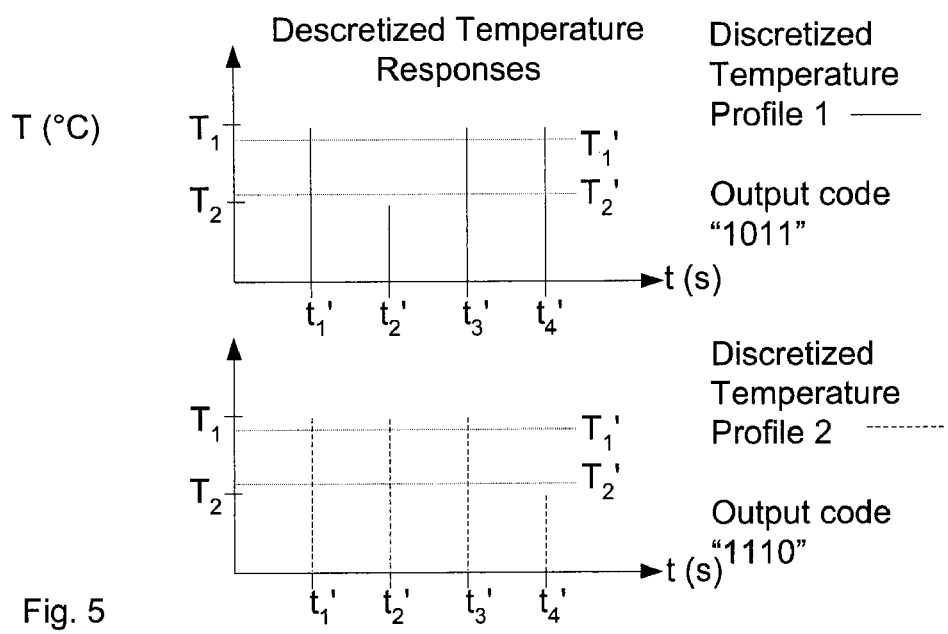
FIG. 5 is an exemplary graph showing discretized temperature responses, which correspond to the temperature profiles of FIG. 4, and which are encoded according to an embodiment of the invention.

In one particular embodiment, as an example of such an analysis, temperature measurements are taken periodically (e.g. $t_1'$, $t_2'$, $t_3'$, and $t_4'$ in FIG. 5) in accordance with a predetermined time interval, $\Delta t_a$, before or after times at which changes occur in the output profile (e.g. $t_1$, $t_2$, $t_3$, and $t_4$ in FIG. 3). In the example of FIGS. 3 and 4, FIG. 5 shows the discrete temperature responses at times $t_1'$, $t_2'$, $t_3'$, and $t_4'$ for each of the temperature profiles shown in FIG. 4. Variable temperature thresholds $T_1'$ and $T_2'$ are set, within the controller, above or below which the discrete temperature response at a given $t_n'$ is assigned a certain digitized value. These thresholds may be adjusted in order to determine the unknown association between probes 102 and pumps 101. In the example of FIG. 5, any response with a value above temperature threshold $T_1'$ is assigned a value of 1 and any response with a value below temperature threshold $T_2'$ is assigned a value of 0. Thus, the measurements made by one temperature sensor are translated from a graphically representable set of measurements or temperature profile, as in FIG. 4, into a digitized output code, as in FIG. 5. As shown in FIG. 5, the measurements made by temperature sensor 1 correspond to the output code 1011 and the measurements made by temperature sensor 2 correspond to the output code 1110. The temperature thresholds ($T_1'$, $T_2'$ or $T_n'$ generally) may be adjusted up or down in order to adjust the sensitivity of the digitization. The resulting output codes are compared to expected codes for each output profile. Comparing FIGS. 3, 4, and 5, output profile 1 has an expected code of 1011 and output profile 2 has an expected code of 1110; thus, output profile 1 corresponds to temperature response profile 1 and output profile 2 corresponds to temperature response profile 2. In another embodiment, the temperature thresholds $T_n'$ can depend on the maximum and minimum temperature values of the temperature profiles, for example with a threshold $T_1'$ being a predetermined value, $\Delta T_\beta$ below the maximum measured temperature $T_1$.

Matching the output profile of a pump 101 to the temperature profile of a temperature sensor 104 matches that pump to that sensor. Because, in this embodiment, the temperature sensors 104 are associated in a known way with the internally-cooled probes 102, the results of the matching operations show, for each temperature sensor 104, which pumps 101 are capable of supplying energy to change the temperature of the probes 102 associated with that sensor 104. That is to say, the matching operations map the probes 102 to the pumps 101. A probe 102 can be mapped to one or more pumps 101, or can be mapped to no pumps.

The mapping results of the aforementioned analysis and matching, for each temperature sensor (and its associated probes), may be verified by controller 105. In other words, controller 105 may verify the association between pumps 101 and probes 102 determined by the analysis. For any set of m pumps and p temperature sensors 104, there will be a set of possible results mapping the sensors 104 to the pumps 101 given by the equation: $(mC0+mC1+ \ldots +mCm)\hat{\,}p$, where C represents the Choose function whereby $xCy=x!/(x-y)!y!$. For an embodiment having two pumps 101 and two temperature sensors 104, there are 16 possible mapping outcomes as shown in the following table:

Set of Possible Results for Mapping Two Pumps to Two Temperature Sensors:

|  | Temperature Sensor 1 | Temperature Sensor 2 |
|---|---|---|
| 1) | Pump 1 | Pump 1 |
| 2) | Pump 1 | Pump 2 |
| 3) | Pump 1 | Pumps 1 and 2 |
| 4) | Pump 1 | No Pumps |
| 5) | Pump 2 | Pump 1 |
| 6) | Pump 2 | Pump 2 |
| 7) | Pump 2 | Pumps 1 and 2 |
| 8) | Pump 2 | No Pumps |
| 9) | Pumps 1 and 2 | Pump 1 |
| 10) | Pumps 1 and 2 | Pump 2 |
| 11) | Pumps 1 and 2 | Pumps 1 and 2 |
| 12) | Pumps 1 and 2 | No Pumps |
| 13) | No Pumps | Pump 1 |
| 14) | No Pumps | Pump 2 |
| 15) | No Pumps | Pumps 1 and 2 |
| 16) | No Pumps | No Pumps |

In this embodiment, controller 105 performs verifying operations either accepting or rejecting the combined mapping from the matching operation. Verification criteria 210 can be changeable, for example by utilizing software such as verifying block 214 with comparative mapping, and will depend on the requirements of the treatment or system. Any particular mapping result or any group of mapping results may be chosen as comparative mappings to define verification criteria 210 as a basis for accepting or rejecting the combined mapping from the mapping operation, such as, for example, rejecting any mapping result where a temperature sensor 104 is not mapped to any pump 101.

As well, if the controller rejects the mapping determined by the aforementioned analysis and matching operations, the specific results of the matching operations can be used to modify the output profile of the pumps 101 during repetitions of the mapping operations, if any. For example, if the verifying block 214 requires that every pump 101 be matched to a different temperature sensor 104, then the output profile of an unmatched pump 101, or of a pump 101 that is matched to multiple temperature sensors 104, can be modified to make it more distinguishable (e.g. by increasing the magnitude of the changes in pump rate, or by separating it from other output profiles in time). Characteristics of the matching operations can also be changed depending on the results of the verification operation. For example, if a temperature sensor 104 is shown to be matched to more than one pump 101, in a situation where each temperature sensor 104 is required to be connected to only one pump 101, decreasing the tolerance of the matching operation to changes in temperature can allow the correct match to be determined above any background temperature fluctuation.

Referring now to FIG. 6A, there is shown a system 600 according to a first generalized embodiment of the present invention. In such embodiments, the association(s) between at least one energy delivery device 602 and at least one measuring device 604 is known, while the association(s) 603 between at least one energy delivery device 602 and at least one energy source 601 is unknown and may be determined using embodiments of a method aspect of the present invention. As noted with respect to FIG. 1, measuring devices 604 are connected to controller 605 via connections 606.

In one particular exemplary embodiment of the system 600 shown in FIG. 6A, system 600 comprises a single energy source 601 which may be, for example, a pump as described herein above. In addition, system 600 comprises a plurality of energy delivery devices 602, which may be, for example, probes as described herein above. In one specific embodiment, system 600 comprises at least two internally-cooled probes connected in series to the pump. In other words, both of the probes are connected to the same pump, with the pump output connected to one probe, the output of that probe connected to the input of the next probe and the output of the final probe connected back to the pump input. In this embodiment, while it is known that all probes are connected to the same pump, the order in which they are connected in series is unknown and may be determined in accordance with embodiments of the present invention, described further herein below. It would be useful to know the order in which the probes are connected because the probes that are connected proximate to the pump in the series of probes will be cooled to a greater degree than probes in the series of probes that are connected more remotely from the pump (since the coolant has absorbed heat from the proximate probes). In such a situation, the controller 605 may, for example, operate the least-cooled probe as a return electrode since the current density around that probe would not be as high as the current density around the other probes due to inherent losses in the electrical system.

In an alternate exemplary embodiment of system 600, system 600 comprises at least two energy sources 601, for example two pumps. In addition, system 600 comprises a single energy delivery device 602, for example a single internally-cooled probe. In one such embodiment, it is known that the probe is only connected to a single pump but it is unknown (by the controller 605) which pump is connected to the probe, since both pumps are operatively coupled to the controller 605. In this embodiment, controller 605 may determine which pump is associated with the probe using an embodiment of the method aspect of the present invention, described further herein below.

Referring now to FIG. 6B, there is shown a system 610 according to a first generalized embodiment of the present invention. In such embodiments, the association(s) between at least one energy delivery device 602 and at least one energy source 601 is known, while the association(s) 603 between at least one energy delivery device 602 and at least one measuring device 604 is unknown and may be determined using embodiments of a method aspect of the present invention. Again, as noted with respect to FIG. 1, measuring devices 604 are connected to controller 605 via connections 606.

In one particular exemplary embodiment of the system 610 shown in FIG. 6B, system 610 comprises a single energy source 601, for example a single electrical generator. Furthermore, in this particular embodiment, system 610 comprises a plurality of energy delivery devices 602, for example two electrosurgical probes. In addition, this embodiment of system 610 comprises a plurality of measuring devices 604, for example two thermocouples, whose associations with the probes are unknown. In other words, while the connections between energy sources 601 and energy delivery devices 602 are known, it is unknown which thermocouple is measuring a change in temperature due to which probe. For example, in one such embodiment, the two thermocouples comprise separate and distinct temperature probes that are not integral with the energy delivery probes, for example for measuring the temperature of tissue away from the probes. However, as noted herein above, each temperature probe is capable of sensing and measuring a change in the property of a tissue resulting from energy delivery by at least one of the probes. In this embodiment, controller 605 may determine which thermocouple is associated with which probe using an embodiment of the method aspect of the present invention, for example by delivering energy to a probe and measuring a response with the thermocouples.

As described above, a wide variety of devices may be used as energy sources 601, energy delivery devices 602 and measuring devices 604 in systems that, for example, treat tissue by applying energy. In some embodiments, for example, one or more of the energy sources 601 comprise an electrosurgical generator for generating electrical energy. In particular embodiments, the electrosurgical generator is operable to deliver electrical energy in the radiofrequency range. In addition, embodiments of the invention described herein are intended to encompass automatic mapping to determine connections 603 between at least one energy delivery device 602 and one of at least one measuring device 604 and at least one energy source 601 for any and all such systems, and any methods for such mapping. Additionally, while systems for controlling the output from the energy source or sources 601, receiving input from the measuring devices 604 via connections 606, and mapping the energy delivery devices 602 to the energy sources 601 or measuring devices 604, are all considered to be components of the controller 605, they are not required to be collected within one self-contained device.

Figure 7:
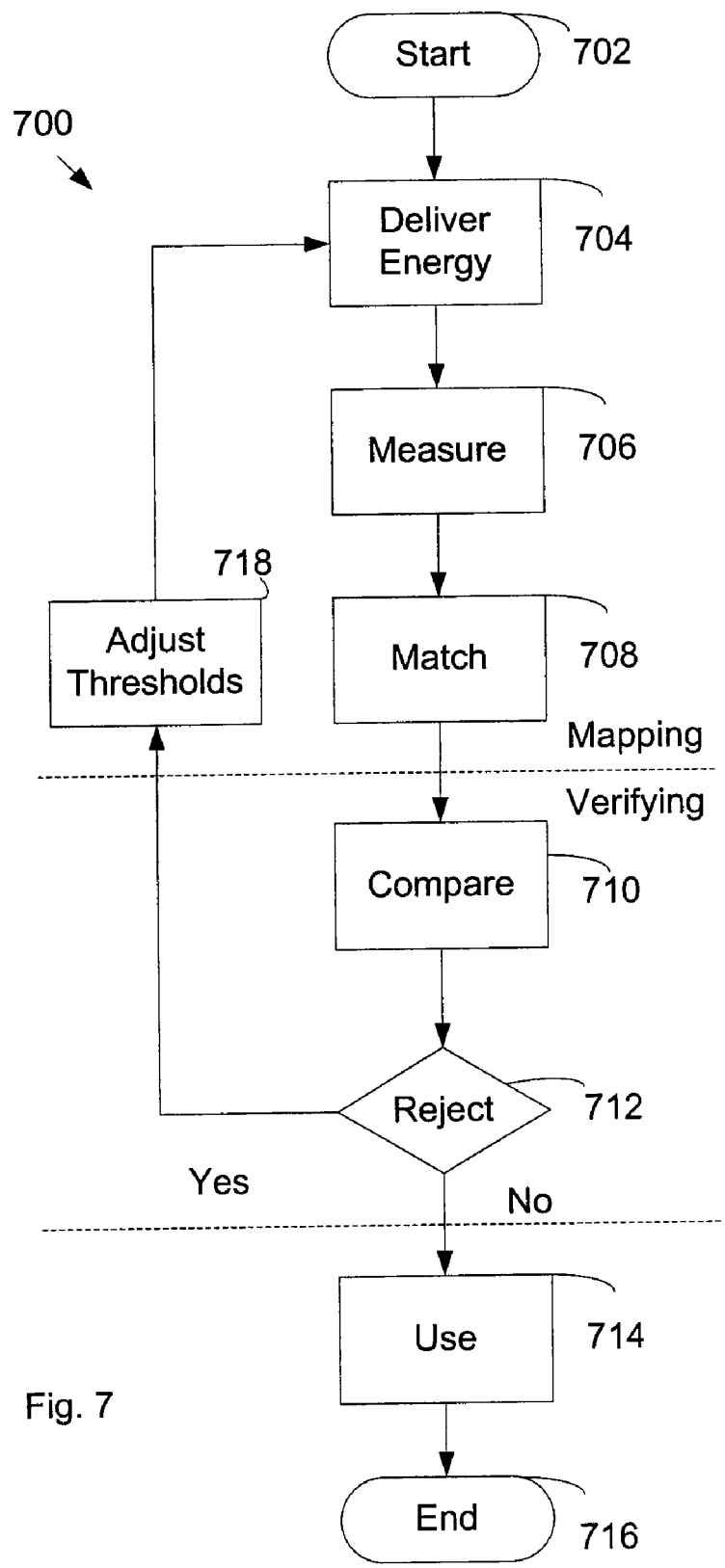
FIG. 7 is a flowchart of operations for mapping in accordance with an embodiment of the invention.

Referring now to FIG. 7, a generalized embodiment of a method aspect of the present invention is illustrated. FIG. 7 is a flowchart of operations 700 for mapping at least one energy delivery device to one of at least one energy source or at least one measuring device in accordance with an embodiment of the invention for a system to be mapped such as systems 600 or 610. Briefly, commencing at start 702, such as following the initial assembly and general set up of the system, operations 700 initiate a mapping phase and proceed to a verifying phase. In response to the verifying phase, mapping operations 700 may loop back to the mapping phase or continue to a use phase.

More particularly, at step 704, controller 605 operates at least one energy source 601 to deliver energy to at least one energy delivery device 602. In response, at least one measuring device 604 measures a change in a property of the tissue and provides the measured response to the controller 605 (step 706) via connections 606 for determining at least one response profile. As described herein above, the system includes unknown associations 603, between energy delivery devices 602 and energy sources 601 or between energy delivery devices 602 and measuring devices 604, which may be determined. Though steps 704 and 706 are shown as complete, sequential steps, steps 704 and 706 may be repeated for each of energy sources 601 to be mapped or in other manners in accordance with a test procedure.

At step 708, controller 605 matches the at least one energy delivery device 602 to one of at least one energy source 601 or at least one measuring device 604. Typically, step 708 comprises analyzing at least one response profile determined from measuring device 604 in order to determine an unknown association between the at least one energy delivery device 602 and one of the at least one energy source 601 and the at least one measuring device 604. For example, as described previously, this step may comprise matching output profiles of energy sources 601 to response profiles determined by measurements provided by measuring devices 604. In the context of this description, matching output profiles to response profiles encompasses not only an analysis and comparison of a response profile to an output profile, for example as described with respect to FIGS. 3-5, but also includes a more limited analysis, for example, whether or not a response was elicited following energy delivery by energy source 601. In other words, following delivery of energy from energy source 601, controller 605 may simply determine whether or not measuring devices 604 sensed a response, in order to associate an energy delivery device 602 with the energy source 601. In such an embodiment, controller 605 may not necessarily compare the output profile to the response profile but may simply determine whether or not a response was sensed. This may be useful, for example, in embodiments wherein the system comprises a plurality of energy sources 601 and a single energy delivery device 602, as described herein above. In such embodiments, it would be sufficient to determine whether or not delivery of energy from a given source elicits a response from the measuring device associated with the energy delivery device in order to determine which energy source is associated with the energy delivery device.

Alternatively, in some embodiments, more than one response profile is determined, for example if more than one measuring device 604 is utilized. In such embodiments, rather than comparing or matching output profiles to the response profiles, step 708 may comprise an analysis and comparison of the response profiles themselves. For example, in embodiments of a system comprising a single energy source 601 coupled to a plurality of energy delivery devices 602, where it is known, for example, that each energy delivery device 602 is coupled to the same source 601 but where the order of the coupling is unknown, it may not be necessary to compare the output profile of the energy source 601 to the response profiles. Rather, the response profiles themselves may be compared in order to determine, for example, which energy delivery device 602 is more directly coupled to the energy source 601.

At step 710, controller 605 compares the mapping results to verify that the respective associated energy sources 601, measuring devices 604 and delivery devices 602 accord with verification criteria as previously described. At step 712, if the match is accepted (i.e. not rejected), via No branch to step 714, operations may proceed to a use phase and thereafter end (step 716). At step 712, if the match is rejected, via the Yes branch, operations may proceed back to the matching phase, such as to step 718 where tuneable parameters (e.g. various thresholds) may be adjusted. It should be noted that step 718 is optional and, in some embodiments, operations may proceed back to the matching phase without adjusting any parameters. Moreover, though not shown, the system to be mapped may be otherwise manipulated, for example, by repositioning energy delivery devices 602 or measurement devices 604 or by adjusting connections 603. Steps 704-712 may then be repeated as necessary. Alternatively, the operations may end at step 712 if, after a predetermined number of repetitions of steps 704-712, the match is rejected, and a message may be displayed stating that mapping has failed (not shown).

In addition, in some embodiments, the method may further comprise a step of utilizing at least one response profile as an input for determining one or more parameters for energy delivery during a treatment procedure. In other words, as described herein above, if it determined that one probe is being cooled to a lesser degree than other probes due to the fact that it's more remote from a pump in a series of probes, then the controller may operate the system to utilize that probe as a return electrode, thereby reducing the current density and heat generated around that probe.

The output profile, the response profile or a combination thereof, can also be used to determine one or more properties of the tissue, for example the heat capacity of the tissue, around the energy delivering probes, which in turn can be used to modify one or more parameters of energy delivery, for example the PID constants that control the energy delivery algorithm. A selected amount of cooling, for example, can be supplied to the energy delivery probe (and thus to the surrounding tissue) in order to determine the unknown association between pump and probe. However, the response profile sensed from the tissue may also be indicative of a property of the tissue (e.g. heat capacity) that can be used to set parameters of energy delivery during the procedure itself. In the case of heat capacity, for example, the response profile may show a change in temperature over time as a result of the cooling (similar to FIG. 4). By analyzing this curve, the rate of change of temperature in the tissue (reflecting its heat capacity) may be determined. Alternatively, electrical/thermal energy can be delivered to a probe to cause the tissue temperature to rise and the heat capacity of the tissue may then be determined from the temperature decay curve of the tissue. Other tissue properties that may be determined while practicing or ancillary to practicing embodiments of the method of the invention may include, for example, impedance.

Although the exemplary embodiments of a system and method described herein are described in relation to mapping energy delivery devices to sources of energy in the form of electrical energy or cooling carried by a fluid medium, any form of energy, including but not limited to: electrical current or potential, thermal energy, optical energy, pressure or magnetic forces may be added or removed and be considered to be within the scope of this invention. Many tissue properties, both physical and chemical, including but not limited to: temperature, impedance, electrical potential, pressure, density, and opacity can be modulated by a system using energy delivery devices automatically mapped to energy sources. Furthermore, such a system has application in any tissue of the body and for various treatment procedures, for example in a procedure used to treat pain.

It is appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

I claim:

1. An electrosurgical system for controlling the delivery of energy from at least one energy source within a group of energy sources to at least one energy delivery device within a group of energy delivery devices using at least one measuring device within a group of measuring devices, the system comprising:
    an energy source interface for communicating with the at least one energy source operable to deliver energy;
    a measuring interface for receiving measurements indicating a change in a property of a tissue from the at least one measuring device; and
    a mapping subsystem capable of determining an association between the at least one energy delivery device and one of the at least one energy source and the at least one measuring device.

2. The system of claim 1, wherein the mapping subsystem comprises a processor and a memory storing instructions and data for controlling the processor, the instructions and data adapting the processor to associate the at least one energy delivery device with one of the at least one energy source and the at least one measuring device in response to operating the at least one energy source and analyzing a response profile determined using the at least one measuring device.

3. The system of claim 2, wherein the response profile defines a change in a property measured by the at least one measuring device.

4. The system of claim 1, wherein the system is operable to control each energy source in accordance with a respective output profile and to receive at least one measurement defining at least one respective response profile and wherein the mapping subsystem comprises an analyzing component to analyze the at least one response profile to determine the association between the at least one energy delivery device and one of the at least one energy source and the at least one measuring device.

5. The system of claim 4, wherein the analyzing component comprises instructions for matching the output and response profiles.

6. The system of claim 1, wherein the mapping subsystem comprises a verifying component to verify the association between the at least one energy delivery device and one of the at least one energy source and the at least one measuring device.

7. The system of claim 1, wherein the system defines a controller contained within a single device.

8. A system for delivering energy, the system comprising:
    a plurality of energy sources, at least one energy source capable of producing energy according to an output profile that is distinct from the output profile of at least one other energy source;
    a plurality of energy delivery devices, each energy delivery device operatively coupled to one or more of the energy sources for delivering the energy;
    a plurality of measuring devices for measuring changes in a property resulting from the delivery of the energy; and
    a controller operatively coupled to at least one of the measuring devices and to the at least one energy source for controlling the at least one energy source and for determining an association between each energy delivery device and a respective one of the energy sources and a respective one of the measuring devices by analyzing the changes.

9. The system of claim 8, wherein the at least one energy source comprises a pump for controlling the movement of a cooling fluid medium.

10. The system of claim 9, wherein at least one of the energy delivery devices comprises an internally cooled probe capable of being inserted into a body of a patient.

11. The system of claim 10, wherein the probe includes an electrode for ablating the tissue.

12. The system of claim 8, wherein the at least one measuring device comprises at least one thermocouple.

13. The system of claim 8, wherein each measuring device is directly coupled to one or more of the at energy delivery devices.

14. The system of claim 8, wherein the at least one energy source comprises an electrosurgical generator for generating electrical energy.

15. The system of claim 14, wherein the electrosurgical generator is operable to deliver electrical energy in the radiofrequency range.

16. A method for controlling delivery of energy from at least one energy source within a group of energy sources to a tissue via at least one energy delivery device within a group of energy delivery devices operatively coupled to the at least one energy source, the method comprising:
    delivering energy from the at least one energy source;
    obtaining measurements indicating changes in a property of the tissue using at least one measuring device within a group of measuring devices, to determine at least one response profile; and
    analyzing the at least one response profile to determine an association between the at least one energy delivery device and one of the at least one energy source and the at least one measuring device, thereby to control the delivery of energy to the tissue.

17. The method of claim 16, wherein the at least one energy source comprises a pump for pumping a cooling fluid medium.

18. The method of claim 16, wherein the at least one energy delivery device comprises an internally cooled probe capable of being inserted into a body of a patient.

19. The method of claim 16, wherein the energy source comprises an electrosurgical generator for generating electrical energy.

20. The method of claim 16, wherein each measuring device is directly coupled to one or more of the energy delivery devices.

21. The method of claim 16, wherein the step of delivering energy comprises delivering energy from each energy source in accordance with a respective output profile.

22. The method of claim 21, wherein the at least one energy source includes at least two energy sources, energy being delivered from each energy source substantially concurrently.

23. The method of claim 22, wherein the respective output profiles of each energy source differ in at least one parameter selected from the group consisting of fluid flow rate, temperature of cooling medium, voltage, current and power.

24. The method of claim 21, wherein the at least one energy source includes at least two energy sources, energy being delivered from each energy source at least partially sequentially.

25. The method of claim 21, wherein the step of analyzing the at least one response profile comprises matching the output profiles to the at least one response profile.

26. The method of claim 16, wherein at least two response profiles are determined and wherein the step of analyzing the response profiles comprises comparing the at least two response profiles.

27. The method of claim 16, further comprising a step of verifying the association.

28. The method of claim 16, further comprising a step of adjusting a threshold parameter in order to determine the association.

29. The method of claim 16, comprising repeating the method to obtain a correct association.

30. The method of claim 16, wherein the method is used in a procedure for treating pain.

31. The method of claim 16, further comprising a step of utilizing the at least one response profile to determine one or more parameters for energy delivery.

32. A system for delivering energy, the system comprising:
    at least one energy source, each energy source capable of producing energy according to an output profile that is distinct;
    at least one energy delivery device, each delivery device operatively coupled to one or more of the energy sources for delivering the energy, each energy delivery device comprising an internally cooled probe capable of being inserted into a body of a patient;
    at least one measuring device for measuring changes in a property resulting from the delivery of the energy; and
    a controller operatively coupled to the at least one measuring device and to the at least one energy source for controlling the at least one source and for determining an association between each energy delivery device and one of the at least one energy source and the least one measuring device by analyzing the changes.

33. The system of claim 32, wherein the internally cooled probe includes an electrode for ablating the tissue.

34. A method for controlling delivery of energy from at least one energy source to a tissue of a body of a patient via at least one energy delivery device operatively coupled to the at least one energy source, the method comprising:
    inserting the energy delivery device into the body of a patient, the energy delivery device including an internally cooled probe;
    delivering energy from the at least one energy source;
    obtaining measurements indicating changes in a property of the tissue using at least one measuring device, to determine at least one response profile; and
    analyzing the at least one response profile to determine an association between the at least one energy delivery device and one of the at least one energy source and the at least one measuring device, thereby to control the delivery of energy to the tissue.

35. A method for treating pain by controlling delivery of energy from at least one energy source within a group of energy sources to a tissue via at least one energy delivery device within a group of energy delivery devices operatively coupled to the at least one energy source, the method comprising:
    delivering energy from the at least one energy source;
    obtaining measurements indicating changes in a property of the tissue using at least one measuring device within a group of measuring devices, to determine at least one response profile; and
    analyzing the at least one response profile to determine an association between the at least one energy delivery device and one of the at least one energy source and the at least one measuring device, thereby to control the delivery of energy to the tissue and thereby treat pain.

* * * * *

UNITED STATES PATENT AND TRADEMARK OFFICE
CERTIFICATE OF CORRECTION

| | |
|---|---|
| PATENT NO. | : 8,361,063 B2 |
| APPLICATION NO. | : 11/622668 |
| DATED | : January 29, 2013 |
| INVENTOR(S) | : Neil Godara |

Page 1 of 1

It is certified that error appears in the above-identified patent and that said Letters Patent is hereby corrected as shown below:

In the Claims:

Column 13, Line 6, Claim 13 "...one or more of the at energy delivery devices." should read --...one or more of the energy delivery devices.--

Column 14, Line 26, Claim 32 "...one energy source and the least one" should read --...one energy source and the at least one...--

Signed and Sealed this
Twentieth Day of August, 2013

Teresa Stanek Rea
*Acting Director of the United States Patent and Trademark Office*